Figure 1:
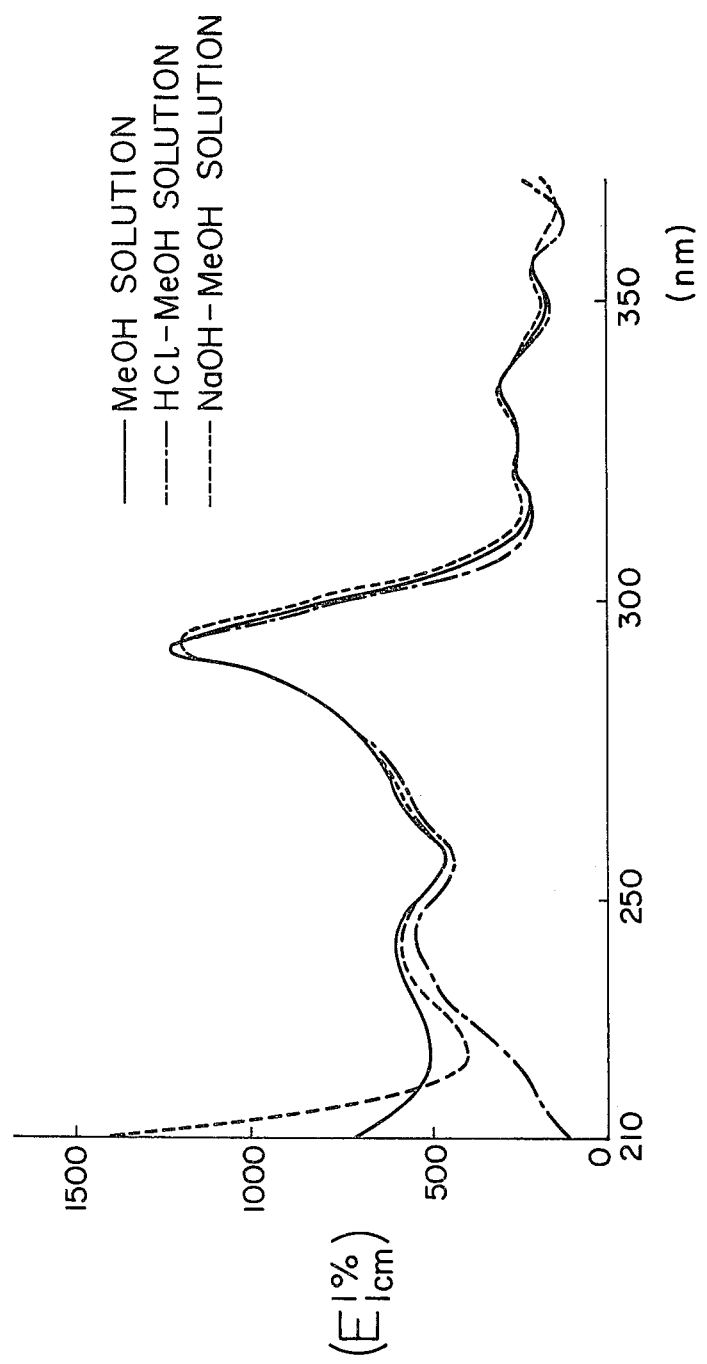

United States Patent [19]

Omura et al.

[11] 4,107,297
[45] Aug. 15, 1978

[54] ANTIBIOTIC COMPOUND

[75] Inventors: Satoshi Omura, Tokyo; Yuzuru Iwai, Narita; Atsushi Hirano, Hasuda, all of Japan

[73] Assignee: The Kitasato Institute, Tokyo, Japan

[21] Appl. No.: 855,379

[22] Filed: Nov. 28, 1977

[30] Foreign Application Priority Data

Dec. 11, 1976 [JP] Japan .................. 51-148299

[51] Int. Cl.$^2$ .............................................. A61K 35/00
[52] U.S. Cl. .................................. 424/122; 195/80 R
[58] Field of Search ........................ 424/122; 195/80 R

[56] References Cited

U.S. PATENT DOCUMENTS 3,843,784  10/1974  Hamill et al. ......................... 424/122
3,845,203  10/1974  Williams et al. ...................... 424/122

FOREIGN PATENT DOCUMENTS 47-10,038  3/1972  Japan ...................................... 424/122

OTHER PUBLICATIONS

Swart et al., Proc. Soc. Explt. Biol. Med., 73 pp. 376–378 (1950).
Science 113, 361–362, 1951.

*Primary Examiner*—Jerome D. Goldberg
*Attorney, Agent, or Firm*—Flynn & Frishauf

[57] ABSTRACT

The present invention relates to a new compound designated as AM-2282, having antibiotic activity and pharmacological activity, and a process of preparing same.

5 Claims, 2 Drawing Figures

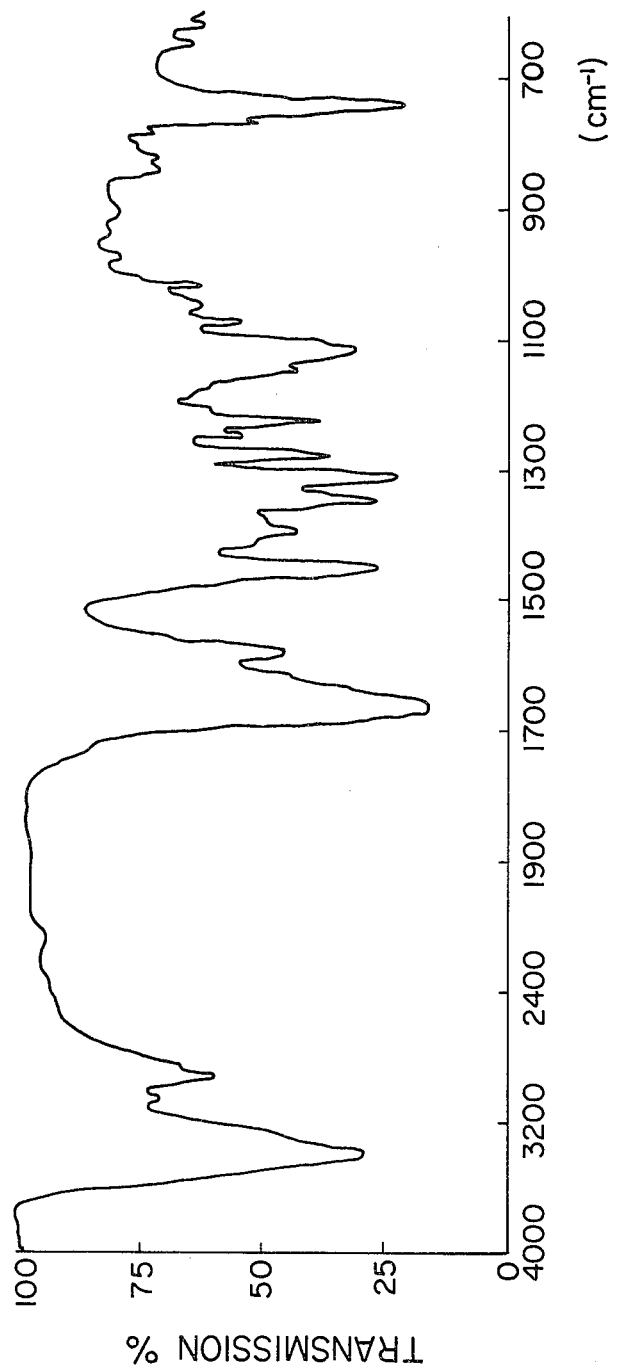

ANTIBIOTIC COMPOUND

The present invention relates to a new compound designated as AM-2282. AM-2282 reveals an antibiotic activity on yeast and fungi, and pharmacological activity on hypertension, edema and ulcer. AM-2282 has therapeutical effect on various infectious diseases caused by a parasite of yeast and fungi, and also has an excellent effect of hypotensive activity. The properties of AM-2282 have been confirmed to be distinguishable from those of the known antibiotic substances such as e.g. oxamicetin and U-24544. AM-2282 is produced by fermentation of a microorganism capable of producing AM-2282 and belonging to the genus Streptomyces in a culture medium.

According to the present invention there is thus provided a product having antibiotic activity and characterized by the following physical and chemical properties:

(1) Elementary analysis:
Carbon, hydrogen, nitrogen and oxygen are contained and neither sulfur nor halogen is contained. Elementary analysis of this substance has given the following values: C: 70.03%, H: 6.03%, N: 11.21%

(2) Molecular weight:
m/e determined by mass spectrum, 466

(3) Molecular formula: $C_{28}H_{26}N_4O_3$
Molecular formula has been determined on the basis of the fact that the aforementioned mass spectrum (m/e, found 466.199, calcd. 466.200 for $C_{28}H_{26}N_4O_3$) indicates the molecular weight to be 466, the fact that NMR spectrum shows the number of protons in the compound to b 25–27, the fact that $^{13}$C-NMR spectrum shows the number of carbon atoms in the compound to be 26–28, and the aforementioned data of elementary analysis. NMR spectrum is referred to in The Journal of Antibiotics, April, 1977, p.281.

(4) Specific rotation:
$[\alpha]_D^{25} = +35.0$ (C=1.0 in methanol)

(5) Melting point:
No clear melting point is shown. The compound turns brown at 208° C and assumes a tarry state at 260° C.

(6) Ultraviolet absorption spectrum:
$\lambda_{max}^{MeOH}nm$ ($E_{1cm}^{1\%}$): 243 (537), 267 (sh. 552), 292 (1288) 322 (sh. 537), 335 (313), 356 (220), 372 (254).
These peaks are not shifted in alkaline and acidic conditions.

(7) Infrared absorption spectrum;
By KBr method, there are absorptions observed at 3450 cm$^{-1}$ due to the presence of amine and hydroxy groups, at 2960 cm$^{-1}$ due to the presence of methyl and methylene groups, of 1675 cm$^{-1}$ due to the presence of carbonyl and double bond groups, at 1588 cm$^{-1}$, 1460 cm$^{-1}$, 1356 cm$^{-1}$, 1322 cm$^{-1}$, 1285 cm$^{-1}$, 1230 cm$^{-1}$, 1123 cm$^{-1}$ and 752 cm$^{-1}$.

(8) Color reaction:
Positive in Dragendorff reaction, Molisch reaction, Rydon-Smith reaction and ninhydrin reagent. Negative in Beilstein reaction, ferric chrolide reagent and aniline phthalate reagent.

(9) Solubility in various solvent:
Soluble in dimethyl sulfoxide and dimethyl formamide. Sparingly soluble in chloroform, ethyl acetate, n-butyl acetate and methanol. Insoluble in petroleum ether, n-hexane and water.

(10) $R_f$ values by chromatography:
Thin layer chromatography using silica gel (Kieselgel G, 0.3 mm, commercially available from Merck Inc., U.S.A.) carried out in conventional manner gave the following $R_f$ values:

| | |
|---|---|
| Chloroform - methanol (10:1 V/V) | 0.55 |
| Benzene - acetone (1:2 V/V) | 0.43 |
| n-Butanol - acetic acid - water (8:1:0.5 V/V) | 0.24 |

The spectrum charts are shown in attached drawings.
FIG. 1 is an ultraviolet absorption spectrum of AM-2282.
FIG. 2 is an infrared absorption spectrum of AM-2282.

Among the various physical and chemical characteristics set forth herein, the UV absorption spectrum is the first to be used for identification purposes. Various known antibiotic substances having analogous characteristics to those of AM-2282, such as oxamicetin [J. Antibiotics, 26, 752, 757, 765 (1973)] and U-24544 [Appl. Microbial., 15, 1142 (1967)] have a UV absorption peak at 280-310 nm. However, UV absorption peak (305 nm) of oxamicetin is shifted to 322 nm in alkaline condition and to 316 nm in acidic condition, respectively. Furthermore, oxamicetin has, in addition to a peak at 322 nm, another peak at 265 nm in alkaline condition.

U-24544 has an absorption maximum at 303 nm, and its peak is shifted to 331 nm in alkaline condition.

In addition to these findings, IR absorption spectrum of AM-2282 is different from that of oxamicetin and U-24544.

It has thus been confirmed that oxamicetin and U-14544 are not identical with AM-2282.

It is therefore no doubt that the antibiotic substance according to the present invention viz. AM-2282 is new and is characterized by its UV absorption spectrum in combination with molecular weight, molecular formula, IR absorption spectrum, and antibacterial spectrum.

AM-2282 reveals an antibiotic activity upon yeast and fungi, and pharmacological activity as hypotensor. More particularly the biological characteristics of AM-2282 according to the present invention are as follows:

Table 1 indicates the antibacterial and antifungal activity of AM-2282 in terms of the minimum inhibitory concentration (mcg/ml) determined by agar dilution method.

Table 1

| The antibacterial spectrum of AM-2282 | | |
|---|---|---|
| Test organism | MIC (mcg/ml) | Medium* |
| Staphylococcus aureus FDA 209P | >200 | N |
| Bacillus substilis PCI 219 | >200 | N |
| Sarcina lutea PCI 1001 | 25 | N |
| Mycobacterium Smegmatis ATCC 607 | 50 | N |
| Escherichia coli NIJH | >200 | N |
| Pseudomonas aeruginosa P-3 | >200 | N |
| Proteus vulgaris IFO 3167 | >200 | N |

Table 1-continued

The antibacterial spectrum of AM-2282

| Test organism | MIC (mcg/ml) | Medium* |
|---|---|---|
| Xanthomonas oryzae | 200 | N |
| Candida albicans | 6.25 | P |
| Candida pseudotropicalis | 3.12 | P |
| Saccharomyces sake | 3.12 | P |
| Aspergillus niger | 25 | P |
| Aspergillus brevipus | 3.12 | P |
| Aspergillus fumigatus | 12.5 | P |
| Trichophyton rubrum | 6.25 | P |
| Trichophyton mentagrophytes | 25 | P |
| Cryptococcus neoformans | 50 | P |
| Microsporum gipseum | >100 | P |
| Sclerotinia cinerea | 0.78 | P |
| Piricularia oryzae | 0.78 | P |

*N: Peptone 0.5 % W/V, meat extract 0.5 % W/V, agar 1.2 % W/V, pH 7.0.
P: Potato extract containing glucose 1.0 % W/V and agar 1.2 % W/V, pH 6.8.

The results of the test for hypertensive effect will be shown below:

To rats (females weighing 200–250 g) bred under fixed conditions prescribed for disposing them to spontaneous hypertension, hydrochloride of AM-2282 is orally administered at varying dose rates indicated in the table below. On lapse of 1, 3 and 5 hours after the administration, the rats are examined for arteriolar pressure (systolic) in the tail.

| | Dose rate (mg/kg) | Degree of hypertension (%) after lapse of: | | |
|---|---|---|---|---|
| | | 1 hr | 3 hrs | 5 hrs |
| Hydrochloride of AM-2282 | 0.16 | −2 | 1 | 1 |
| | 0.16 | 2 | 2 | 2 |
| | 0.3 | 6 | 13 | 12 |
| | 0.3 | 17 | 23 | 11 |
| | 0.63 | 13 | 13 | 25 |
| | 0.63 | 17 | 24 | 24 |
| | 1.25 | 15 | 23 | 31 |
| | 1.25 | 18 | 25 | 39 |
| α-methyl DOPA | 100 | 7 | 13 | 13 |

The hypertensive effect appears at the minimum dose rate of 0.3 mg/kg.

The present antibiotic substance is a basic nitrogen-containing compound, viz. a so-called alkaloid-like substance. In the experiment using rats, it is ascertained to exhibit an activity on edema and ulcer. The minimum effective concentration is established to be 1.0 mg/kg.

The acute toxicity ($LD_{50}$ ip.) of AM-2282 in mice calculated by the Behrens-Karber method is 6.6 mg/kg.

According to a further feature of the present invention, there is provided a process for the preparation of a product as hereinbelow defined which comprises aerobically culturing a microorganism of the genus Streptomyces to accumulate AM-2282 in a culture medium and recovering the said product therefrom.

The process of the present invention is advantageously effected using a microorganism of the species hereinafter described as the strain AM-2282, but any mutant obtained therefrom may also be used.

The microbiological characteristics of the preferred strain AM-2282, for example Streptomyces sp. AM-2282 (FERM-P No. 3725, NRRL 11, 184), used in the following examples are as follows:

1. Morphological characteristics:

Substrate mycelium is developed with simple branching on malt agar media. Aerial mycelium is formed on malt agar media, except for several synthetic media. Spore chain morphology belongs to section Rechiflexibiles. Sporangia, flagellated spores are not observed. Spores are cylindrical or oblong, 0.4–0.6 μm by 1.8–2.4 μm, with smooth surface. Sclerotic granules are produced on some organic agar such as yeast-malt agar and range in diameter, from 10 to 30 μm.

2. Cultural characteristics in various media:

The cultural characteristics shown in Table 3 were observed after the cultivation at 27° C for 10 to 14 days. Aerial mass colors were determined by comparison with Color Hamony Manual (Container Corporation of America, Chicago 1958).

Table 3

Cultural characteristics of strain AM-2283

| Medium | Growth | Reverse | Aerial mycelium | Soluble pigment |
|---|---|---|---|---|
| Sucrose-nitrate agar | good, melon yellow (3ga) | light melon yellow (3ea) | poor, velvety, light melon yellow (3ea) | light melon yellow (3ea) |
| Glucose-nitrate agar | good, wrinkled, melon yellow (3ga) | light melon yellow (3ea) | poor, velvety, light melon yellow (3ea) | light melon yellow (3ea) |
| Glycerol-calcium malate agar | good, light melon yellow (3ea) | pearl pink (3ca) | moderate, velvety, pearl pink (3ca) | — |
| Glucose-asparagine agar (ISP) | good, apricot (4ga) | light apricot (4ea) | moderate, velvety, flesh pink (4ca) | — |
| Glycerol-asparagine agar (ISP) | good, light melon yellow (3ea) | light melon yellow (3ea) | moderate, velvety, white | — |
| Inorganic salts-starch agar (ISP) | good, light melon yellow (3ea) | pearl pink to light tan (3gc) | abundant, velvety, white to pearl pink (3ca) | — |
| Tyrosine agar (ISP) | good, light melon yellow (3ea) | light ivory (2ca) | moderate, velvety, pearl pink (3ca) | — |
| Nutrient agar | good, bamboo (2fb) | maize (2hb) | poor, velvety, ivory tint (2cb) to pearl pink (3ca) | bamboo (2fb) |
| Glucose-peptone agar | moderate, wrinkled, light maize (2ea) | melon yellow (3ga) | moderate, velvety, flesh pink (4ca) | — |
| Yeast extract-malt extract agar (ISP) | good, amber (3pc) | melon yellow (3ia) | moderate, velvety, white to pearl (3ba) | — |
| Oatmeal agar (ISP) | good, light melon yellow (3ea) | light melon yellow (3ea) | moderate, velvety, white to pearl pink (3ca) | — |
| Peptone-yeast extract iron agar (ISP) | good, ivory (2db) | maize (2hb) | — | — |
| Tryptone-yeast extract broth (ISP) | surface growth light ivory (2ca) | | light ivory (2ca) | colonial yellow (2ga) |

ISP: Culture medium formally selected by International Streptomyces Project

3. Physiological characteristics:
   (1) Growth temperature range: 20°–40° C (yeast extract-malt agar medium)
   (2) Formation of melanoid pigment: negative (tryptone-yeast extract, peptone-yeast extract-iron agar, tyrosine agar)
   (3) Liquefaction of gelatin: positive (4) Hydrolyzation of starch: positive
(5) Coagulation of skim milk: suspected positive
(6) Peptonization of skin milk: positive
(7) Formation of hydrogen sulfide: negative
(8) Formation of nitrous acid: negative
(9) Hydrolyzation of cellulose: suspected positive 4. Assimilability of various carbon sources:

The following are results obtained by culturing present strain in Pridham-Gottlief medium.

Assimilable: D-glucose, L-arabinose, Sucrose, L-inositol, D-mannitol.

More or less assimilable: D-fructose, D-xylose, L-rhamnose, cellulose.

From these data, the cultural and physiological characteristics of strain AM-2282 can be summarized as follows: Growth is brownish white to pale yellowish orange or redish yellow; aerial mass color is white, yellowish or pinkish color on various agar media; melanoid pigments are not formed in peptone-yeast-iron agar, tyrosine agar, and tryptone-yeast broth. When these descriptions were compared with those of known series of Streptomyces described in "Bergey's Manual of Determinative Bacteriology (8th, ed.)" and the other sources, an agreement was found in the following five species: *Streptomyces roseofulvus* Pridham et al. 1958, *Streptomyces pluricolorescens* Okami and Umezawa 1961, *Streptomyces moderatus* Reusser 1967, *Streptomyces baarnensis* Pridham et al. 1958 and *Streptomyces tolypophorus* Shibata et al. 1971. However, these strains were distinguished from strain AM-2282 by the following descriptions of their morphological and cultural characteristics.

The spore of *S. roseofulvus* is about 1 $\mu$, and pale grayish yellow or pale brownish gray pigment is found in yeast extract-malt extract agar, oatmeal agar and salts-starch agar. This strain utilizes D-xylose, D-fructose and rhamnose. The spore of *S. pluricolorescens* is also short (about 1 $\mu$) and reverse side of colony appears grayish yellow or yellowish brown on yeast-malt agar, oatmeal agar, salts-starch agar and glycerol-asparagine agar. Aerial mycelium of *S. moderutus* appears grayish yellow pink on yeast-malt agar, oatmeal agar and salts-starch agar, and it produces purple soluble pigment. *S. baarnensis* and *S. tolypophorus* resemble Streptomyces sp. AM-2282 in having long spore. However, *S. baarnensis* has poor aerial mycelia, its color is white to gray on various organic media and reverse side of colony appears light ivory. *S. tolypophorus* has poor and white aerial mycelia, and the reverse side of the colony has no distinctive pigment on salts-starch agar and has an orange yellow pigment on glycelol-calcium-malate agar. In carbon-source utilization notable growth is observed with fructose, xylose and rhamnose.

On the basis of the above data, it is reasonable to conclude that the strain AM-2282 is classified as a new species of Streptomyces, and the name, *Streptomyces staurosporeus* nov. sp. is proposed. The proposed species epithets "stauros" and "spora" and the Greek nouns meaning "stave" and "spore", respectively. This strain has been deposited as Streptomyces sp. AM-2282 with the Fermentation Research Institute, Agency of Industrial Science and Technology, Chiba-ken, Japan (FERM-P No. 3725) and with ARS Culture Collection, Peoria, U.S.A. (NRRL 11,184).

It is also possible to obtain a mutant strain thereof for example in conventional manner using ultraviolet ray, X-ray, radiation, chemicals and the like. A mutant strain which is obtained by treatment with ultraviolet ray in a conventional manner shows an excellent productivity. The AM-2282 producing strain used in the following examples is capable of producing AM-2282 in the cultured broths, viz. both in the cultured liquor and in the microbial bodies.

According to the present process, any synthetic or organic medium may be used when it contains a suitable source of carbon, nitrogen and inorganic substances. If desired, various other nutrients which are conventionally used for culturing various microorganisms belonging to the genus Streptomyces may be added.

As the carbon source, it is possible to use various materials which contain assimilable carbon, preferably such as glucose, maltose, lactose, succharose, starch, dextrine, glycerin, molasses and the like.

As the nitrogen sources, it is possible to use various materials which contain assimilable nitrogen, preferably such as soybean meal, corn steep liquor, cotton seed cake, peptone, meat extract, yeast extract, yeast, casein hydrolyzate, ammonium salts, nitrates and the like.

Inorganic substances, for example, various phosphates (magnesium sulfate and the like) and various salts of the calcium, sodium, iron, manganese, and the like may also be used to control the medium.

Liquid medium is preferred for producing a large amount of AM-2282. However, a solid medium may also be used. It is possible to use a seed medium having a similar composition to that of the main culture medium. The seed is preferably obtained by fermentation carried out aerobicablly at a temperature of about 27° C for 1 or 2 days, for example, a Sakaguchi flask.

The fermentation is carried out under aerobic conditions with shaking at a temperature of from 15° to 40° C (preferably from 25° C to 30° C) at pH of from 6 to 10 (preferably from 6 to 7) for 50 to 120 hours, whereby a large amount of AM-2282 is accumulated concurrently in the medium and microbial bodies. After completion of the fermentation, AM-2282 is recovered from the cultured broths by known method for separation of an antibiotic substance. For example, the broths are separated into the microbial bodies and filtrate by filtration. And it is also possible to recover AM-2282 without separation of the cultured broths. Such preferable method is based on the above physical and chemical characteristics, that is, AM-2282 is soluble in fat. Namely, the method conventionally used to recover various antibiotic substances of this type, such as, the solvent extraction method is preferably used to recover AM-2282.

On preferred process for the isolation and purification of the antibiotic substance AM-2282 from the cultured broth will be described below:

Cultured broths are adjusted to an alkaline pH (about 10) with ammonia water and then extracted with a suitable organic solvent such as e.g. n-butyl acetate. The extract obtained is concentrated in vacuo to a small volume and then transferred into aqueous 0.1N-HCl. The water layer is subsequently adjusted to pH 10 with ammonia water and extracted with ethyl acetate. The extract obtained is concentrated in vacuo to dryness. After this, the dried material is chromatographed on silica gel with a chloroform-methanol (60:1 V/V) system. The active fractions containing AM-2282, which give positive test on Dragendorff reagent and whose $R_f$ value is 0.55 on silica gel thin-layer chromatography eluted with chloroform-methanol (10:1 V/V) are collected and evaporated to dryness in vacuo to yellowish powder. The powder is recrystallized from chloroform-methanol (100:2, V/V) mixture to afford pale yellow needles of AM-2282.

The determination of the produced antibiotic substance AM-2282 was made by the precipitation test using Dragendorff reagent and the measurement of absorbance at 292 nm on a spectrophotometer.

The following examples illustrate the present invention.

EXAMPLE 1

A culture medium (pH 7.0; 1000 ml) containing glucose (2.0% W/V), peptone (0.5% W/V), meat extract (0.5% W/V), dry yeast (0.3% W/V), NaCl (0.5% W/V) and calcium carbonate (0.3% W/V) was put in a 500 ml Sakaguchi flask as a seed medium. The media were sterilized at a temperature of 120° C for 15 min. One platinum loop of *Streptomyces staurosporeus*, i.e. Streptomyces sp. AM-2282 (FERM-P No. 3725; NRRL 11,184) was taken from a slant culture and inoculated to the seed medium for culturing at a temperature of 27° C for 48 hours with a reciprocating vibrator operated at a rate of 110 r.p.m.

The thus-obtained seed culture was inoculated to the AM-2282 producing medium (pH 7.0; 20 l) containing starch (2.0% W/V), glucose (1.0% W/V), peptone (0.5% W/V), yeast extract (0.5% W/V) and calcium carbonate (0.4% W/V) put in a 30 l jar fermentor. The fermentation was carried out at a temperature of 27° C for 75 hours with shaking (250 rpm) and aeration of 10 l/minute. After completion of the fermentation, the cultural broths (17 l) was adjusted to a pH of 10 with ammonia water. n-Butyl acetate (8 l) was added and the cultural broths were mixed for 30–60 min. at room temperature.

The n-butyl acetate layer was taken out and then transferred into aqueous 0.1N-HCl (2 l). The water layer was subsequently adjusted to pH 10 with 28% ammonia water and extracted twice with ethyl acetate (1 l). The ethyl acetate layer was concentrated under reduced pressure to give brownish coagulant (about 1.3 g) which was washed with ethyl ether (50 ml) to remove fatty impurities. The dried material was transferred to a column packed with silica gel 12 g of Kieselgel 60, a commercial product of Merck Inc., (Rahway, New Jersey, U.S.A.) and developed with a solvent system of chloroform-methanol (400 ml; 60:1 V/V). The eluate was divided into individual fractions (each 2.5 ml). Each fraction was then quantitively determined by means of chemical assay using Dragendorff reagent and also by relying upon a $R_f$ value of 0.55 obtained by a thin layer chromatography (Silica gel 0.3 mm of Kieselgel G. a commercial product of Merck Inc.,) using a solvent system of chloroform-methanol (10:1 V/V). Fractions Nos. 61 to 140 were combined as active fractions and concentrated to dryness under reduced pressure to give yellow powders (170 mg). The powders were dissolved in a small amount (7 ml) of a mixture of chloroform and methanol (98:2)(V/V) and allowed to stand in a cold place over night to obtain pale yellow needles (110 mg) having a purity of more than 99%. The needles had the same characteristics as mentioned before.

When 50 mg of the pale yellow needles were dissolved in chloroform and hydrochloric acid gas was blown into the resultant solution, there was obtained 42 mg of AM-2282 hydrochloride.

EXAMPLE 2

A strain of *Streptomyces staurosporeus* (FERM-P No. 3725 NRRL 11,184) was seed-cultured in a similar manner to that described in Example 1. The obtained seed cultures (600 ml) were also inoculated to same producing-medium (70 l) to that described in Example 1 put in a 100 l jar fermentor. The fermentation was carried out at a temperature of 27° C for 68 hours with shaking (200 rpm) and aeration of 30 l/min. After completion of the fermentation, the cultural broths (63 l) having an adjusted to pH 10 with 28% ammonia water were extracted by adding n-butyl acetate (30 l). The n-butyl acetate layer was taken out and transferred into aqueous 0.1N-HCl (8 l). The water layer was adjusted to pH 10 with 28% ammonia water and again extracted twice with ethyl acetate (4 l).

The ethyl acetate layer was concentrated under reduced pressure to give brownish coagulant (1.4 g) which was washed with ethyl ether (100 ml) to remove fatty impurities. The dried material was treated with a column chromatography in the same manner as Example 1. Fractions No. 41 to 80 (each fraction: 15 ml) were an active fraction which give positive Dragendorff reaction and also have $R_f$ value of 0.55 obtained by same thin layer chromatography of Example 1.

The active fractions were combined and concentrated under reduced pressure to give yellow powder (520 mg). The powder were dissolved in a small amount of chloroform and allowed to stand in a cold place over night. The pale yellow needls of AM-2282 (370 mg) was obtained which had a purity of more than 99%. The characteristics of the product were identical with those of Example 1.

What is claimed is:

1. An antibiotic having the following characteristics
(1) Elementary analysis:
Found: C, 70.03%; H, 6.03%; N, 11.21%;
(2) Molecular weight:
m/e determined by mass spectrum, 466;
(3) Molecular formula: $C_{28}H_{26}N_4O_3$;
(4) Specific rotation: $[\alpha]_D^{25} = +35.0$ (C = 1.0 in methanol);
(5) Melting point: No clear melting point is shown; The compound turns brown at 208° C and assumes a tarry state at 260° C;
(6) Ultraviolet absorption spectrum (FIG. 1):
$\lambda_{max}^{MeOH}nm$ ($E_{1cm}^{1\%}$): 243 (537), 267 (sh. 552), 292 (1228), 322 (sh. 537), 335 (313), 356 (220) 372 (254);
These peaks are not shifted in alkaline and acidic conditions;
(7) Infrared absorption spectrum (FIG. 2): By KBr method, there are absorptions observed at 3450 $cm^{-1}$ due to the presence of amine and hydroxy groups, at 2960 $cm^{-1}$ due to the presence of methyl and methylene groups, at 1675 $cm^{-1}$ due to the presence of carbonyl and double bond groups, at 1588 $cm^{-1}$, 1460 $cm^{-1}$, 1356 $cm^{-1}$, 1322 $cm^{-1}$, 1285 $cm^{-1}$, 1230 $cm^{-1}$, 1123 $cm^{-1}$ and 752 $cm^{-1}$;
(8) Color reaction: Positive in Dragendorff reaction, Molisch reaction, Rydon-Smith reaction and ninhydrin reagent. Negative in Beilstein reaction, ferric chloride reagent and aniline phthalate reagent;
(9) Solubility in various solvents: soluble in dimethyl sulfoxide and dimethyl formamide; sparingly soluble in chloroform, ethyl acetate, n-butyl acetate and methanol; insoluble in petroleum ether, n-hexane and water;

(10) $R_f$ values by chromatography: Thin layer chromatography using silica gel (Kieselgel G, 0.3 mm, commercially available from Merck Inc., U.S.A.) carried out in conventional manner gave the following $R_f$ values:

| Chloroform - methanol (10:1 V/V) | 0.55 |
|---|---|
| Benzene - acetone (1:2 V/V) | 0.43 |
| n-Butanol - acetic acid - water (8:1:0.5 V/V) | 0.24 |

2. A process for producing the antibiotic defined by claim 1 which comprises cultivating the organism Streptomyces sp. AM-2282 (FERM-P No. 3725, NRRL 11,184), in a culture medium containing assimilable sources of carbon, nitrogen and inorganic salts, under aerobic fermentation conditions until a substantial amount of antibiotic activity is produced by said organism in said culture medium, and recovering said antibiotic from said culture medium.

3. A process for producing the antibiotic defined by claim 1 which comprises cultivating the organism Streptomyces sp. AM-2282 (FERM-P No. 3725, NRRL 11,184), in a culture medium containing assimilable sources of carbon, nitrogen and inorganic salts, under aerobic conditions at a temperature of from about 15° to about 40° C, a pH of from about 6 to about 10 and for from about 50 to about 120 hours, and recovering said antibiotic from said culture medium.

4. The process of claim 3, wherein the temperature is from 25° to 30° C.

5. The process of claim 3, wherein the pH is from 6 to 7.

* * * * *

UNITED STATES PATENT AND TRADEMARK OFFICE
CERTIFICATE OF CORRECTION

PATENT NO. : 4,107,297
DATED : August 15, 1978
INVENTOR(S) : SATOSHI OMURA et al It is certified that error appears in the above-identified patent and that said Letters Patent are hereby corrected as shown below:

Column 2, lines 44 and 45 - "U-14544" should be --U-24544--.

Column 3, line 17 - "hypertensive" should be --hypotensive--.

Column 3, line 28 (in table heading) - "hypertension should be --hypotension--.

Column 3, line 64 - "hypertensive" should be --hypotensive--.

Column 8, line 30 - "were" should be --was--.

Column 8, line 32 - "needls" should be --needles--.

Signed and Sealed this

Tenth Day of July 1979

[SEAL]

Attest:

LUTRELLE F. PARKER
Attesting Officer   Acting Commissioner of Patents and Trademarks